United States Patent
Lai et al.

(10) Patent No.: US 11,877,800 B2
(45) Date of Patent: Jan. 23, 2024

(54) METHOD AND SYSTEM FOR DETECTING BLEPHAROPTOSIS

(71) Applicants: Kaohsiung Medical University, Kaohsiung (TW); NATIONAL SUN YAT-SEN UNIVERSITY, Kaohsiung (TW)

(72) Inventors: Chun-Sheng Lai, Kaohsiung (TW); Yi-Wu Chiang, Kaohsiung (TW)

(73) Assignees: KAOHSIUNG MEDICAL UNIVERSITY, Kaohsiung (TW); NATIONAL SUN YAT-SEN UNIVERSITY, Kaohsiung (TW)

( * ) Notice: Subject to any disclaimer, the term of this patent is extended or adjusted under 35 U.S.C. 154(b) by 545 days.

(21) Appl. No.: 17/263,428

(22) PCT Filed: Jul. 27, 2018

(86) PCT No.: PCT/CN2018/097367
§ 371 (c)(1),
(2) Date: Jan. 26, 2021

(87) PCT Pub. No.: WO2020/019286
PCT Pub. Date: Jan. 30, 2020

(65) Prior Publication Data
US 2021/0298595 A1    Sep. 30, 2021

(51) Int. Cl.
*A61B 3/113* (2006.01)
*A61B 3/00* (2006.01)
*A61B 3/11* (2006.01)

(52) U.S. Cl.
CPC ............ *A61B 3/113* (2013.01); *A61B 3/0025* (2013.01); *A61B 3/0058* (2013.01); *A61B 3/11* (2013.01)

(58) Field of Classification Search
CPC ..... A61B 3/113; A61B 3/0025; A61B 3/0058; A61B 3/11; A61B 3/14; A61B 5/00
USPC ......................................................... 351/206
See application file for complete search history.

(56) References Cited

U.S. PATENT DOCUMENTS

| | | | | |
|---|---|---|---|---|
| 2001/0056228 A1* | 12/2001 | Utsugi | ................. | A61B 5/0013 600/300 |
| 2013/0236091 A1* | 9/2013 | Ubillos | ............... | G06F 3/04845 382/163 |
| 2013/0236093 A1* | 9/2013 | Gatt | ...................... | G06F 3/0482 382/311 |

(Continued)

FOREIGN PATENT DOCUMENTS

| CN | 101264007 A | 9/2008 |
|---|---|---|
| CN | 105559802 A | 5/2016 |

*Primary Examiner* — Mohammed A Hasan
(74) *Attorney, Agent, or Firm* — WPAT, P.C

(57) ABSTRACT

A method and a system for detecting blepharoptosis are disclosed. The method and the system include image capturing via a camera to generate three eye images; executing an image processing on the eye images to generate the corresponding border images; executing an image computing on the eye image and the corresponding border image to obtain a plurality of characteristic variables; performing a calculation according to the plurality of characteristic variables to obtain a characteristic parameter set; and comparing the characteristic parameter set with a preset blepharoptosis criteria information to obtain a blepharoptosis severity and a levator function.

10 Claims, 4 Drawing Sheets

(56) References Cited

U.S. PATENT DOCUMENTS

| | | | |
|---|---|---|---|
| 2014/0152792 A1* | 6/2014 | Krueger | A61B 5/4863 |
| | | | 348/78 |
| 2014/0201126 A1* | 7/2014 | Zadeh | A61B 5/165 |
| | | | 706/52 |
| 2018/0249151 A1* | 8/2018 | Freeman | G16H 30/40 |
| 2021/0093189 A1* | 4/2021 | Straub | G16H 30/20 |

* cited by examiner

METHOD AND SYSTEM FOR DETECTING BLEPHAROPTOSIS

FIELD OF TECHNOLOGY

Background of the Invention

1. Field of the Invention

The present invention relates to a detection method and system and, more particularly, to a method and a system for detecting blepharoptosis, which may derive related data for determining blepharoptosis by a machine vision technology, and derive the blepharoptosis severity and whether the levator function is normal according to the data.

2. Description of the Related Art

Blepharoptosis can be classified into congenital blepharoptosis and acquired blepharoptosis. One of the causes of congenital blepharoptosis is maldevelopment of the levator muscle since birth, while one of the causes of acquired blepharoptosis is levator muscle attenuation or dehiscence, which results in that an upper eyelid cannot be lifted to a normal height. Moreover, the visual field is impaired by the ptotic eyelids, symptoms such as forehead wrinkles, neck and shoulder ache, backache, or eyestrain are further caused by the fact that the patient is likely to lift up eyebrows or chin unconsciously in order to lift the upper eyelid.

A conventional surgical method for treating blepharoptosis depends on the degree of blepharoptosis severity and the state of the levator function (LF). Therefore preoperative evaluation of the blepharoptosis conditions is of paramount importance for appropriate correction of the ptosis. The clinicians manually measures the static and eyelid dynamic positions of the involved eyelids by using a ruler, so as to obtain the margin reflex distance 1 (MRD1) from a pupil center point to a center point of the upper eyelid inferior margin curve, margin reflex distance 2 (MRD2) from the pupil center point to a center point of the lower eyelid superior margin curve, ptosis severity, levator function and other related data respectively. Moreover, the doctor also needs manually measure the data including MRD1, MRD2, ptosis severity, and LF again at regular intervals by using the ruler to evaluate the postoperative outcomes.

However, the above-mentioned conventional blepharoptosis detection method takes a lot of time to measure the margin reflex distance 1 (MRD1) from the pupil center point to the center point of the upper eyelid inferior margin curve, the margin reflex distance 2 (MRD2) from the pupil center point to the center point of the lower eyelid superior margin curve, the ptosis severity, the levator function and other related data, and the measurements by different doctors are inconsistent, thereby easily causing an error of the measurement results.

In light of this, it is necessary to improve the conventional blepharoptosis detection method.

SUMMARY OF THE INVENTION

In order to solve the above-mentioned problems, it is an objective of the present invention to provide a method for detecting blepharoptosis, which may obtain related data for determining blepharoptosis by a machine vision technology, and obtain a blepharoptosis severity and whether a levator function is normal according to the data.

It is another objective of the present invention to provide a system for detecting blepharoptosis, which is capable of inferring related data for determining blepharoptosis through an image processing and a machine vision, and automatically detecting whether a levator function is normal and detecting a blepharoptosis severity according to the data.

The method for detecting blepharoptosis of the present invention includes image capturing via a camera to generate three eye images; executing an image processing on the eye images to generate the corresponding border images; executing an image computing on the eye images and the corresponding border images to obtain a plurality of characteristic variables; performing a calculation according to the plurality of characteristic variables to obtain a characteristic parameter set; and comparing the characteristic parameter set with a preset blepharoptosis criteria information to obtain a blepharoptosis severity and a levator function.

The system for detecting blepharoptosis of the present invention includes a photography unit configured to capture three eye images; a storage unit configured to store a preset blepharoptosis criteria information; and a processing unit coupled to the photography unit and the storage unit. The processing unit executes an image processing on the eye images to generate the corresponding border images, the processing unit executes an image computing on the eye images and the corresponding border images to obtain a plurality of characteristic variables, and the processing unit performs a calculation according to the plurality of characteristic variables to obtain a characteristic parameter set, and compares the characteristic parameter set with the preset blepharoptosis criteria information to obtain a blepharoptosis severity and a levator function.

Accordingly, the method and the system for detecting blepharoptosis of the present invention can obtain a patient eye information by an image processing technology in cooperation with a machine vision, obtain the related data for determining blepharoptosis according to the eye information, and automatically detect a levator function and detecting a blepharoptosis severity according to the data. Thus, purposes of convenient operation, great shortening of measurement time, and improvement of measurement consistency may be achieved.

In an example, the three eye images include a pupil image gazing forward, a pupil image gazing upward to the maximum extent, and a pupil image gazing downward to the maximum extent, respectively. Thus, the method for detecting blepharoptosis of the present invention can achieve an effect of detecting a blepharoptosis severity and a levator function at the same time.

In an example, the plurality of characteristic variables includes position coordinates of an eye profile region, a sclera region, an iris region, a pupil region, a pupil center point, an upper eyelid inferior margin curve, a lower eyelid superior margin curve, a center point of the upper eyelid inferior margin curve and a center point of the lower eyelid superior margin curve, respectively. Thus, the method for detecting blepharoptosis of the present invention can achieve an effect of providing relatively complete static measurement parameters and dynamic measurement parameters to detect a blepharoptosis severity and a levator function at the same time.

In an example, the plurality of characteristic variables further includes position coordinates of a canthus left margin point and a canthus right margin point, respectively. Thus, the method for detecting blepharoptosis of the present invention can achieve an effect of determining a blepharoptosis severity and a levator function with assistance of the above parameters.

In an example, the characteristic parameter set includes a ptosis severity between an iris diameter and a palpebral fissure height, as well as a maximum displacement when a pupil moves upwards or downwards to the maximum extent. Thus, the method for detecting blepharoptosis of the present invention can achieve an effect of detecting a blepharoptosis severity and a levator function at the same time.

In an example, the characteristic parameter set further includes a first distance between the pupil center point and the center point of the upper eyelid inferior margin curve, a second distance between the pupil center point and the lower eyelid superior margin intersection point, the palpebral fissure height between the center point of the upper eyelid inferior margin curve and the center point of the lower eyelid superior margin curve, a palpebral fissure width between the canthus left margin point and the canthus right margin point, as well as an ocular surface area derived and calculated according to the iris region. Thus, the method for detecting blepharoptosis of the present invention can achieve the effect of determining a blepharoptosis severity and a levator function with assistance of the above parameters.

In an example, according to the plurality of characteristic variables, a virtual digital eye is formed, and the virtual digital eye overlaps each eye image to analyze whether a huge deviation is generated between the virtual digital eye and the eye image. Thus, the method for detecting blepharoptosis of the present invention can achieve an effect of improving detection accuracy.

In an example, the three eye images include a pupil image gazing forward, a pupil image gazing upward to the maximum extent, and a pupil image gazing downward to the maximum extent, respectively. Thus, the system for detecting blepharoptosis of the present invention can achieve an effect of detecting a blepharoptosis severity and a levator function at the same time.

In an example, the plurality of characteristic variables includes position coordinates of an eye profile region, a sclera region, an iris region, a pupil region, a pupil center point, an upper eyelid inferior margin curve, a lower eyelid superior margin curve, a center point of the upper eyelid inferior margin curve and a center point of the lower eyelid superior margin curve, respectively. Thus, the system for detecting blepharoptosis of the present invention can achieve an effect of providing complete static measurement parameters and dynamic measurement parameters to detect a blepharoptosis severity and a levator function at the same time.

In an example, the plurality of characteristic variables further includes position coordinates of a canthus left margin point and a canthus right margin point, respectively. Thus, the system for detecting blepharoptosis of the present invention can achieve an effect of determining a blepharoptosis severity and a levator function with assistance of the above parameters.

In an example, the characteristic parameter set includes a ptosis severity between an iris diameter and a palpebral fissure height, as well as a maximum displacement when a pupil moves upwards or downwards to the maximum extent. Thus, the system for detecting blepharoptosis of the present invention can achieve an effect of detecting a blepharoptosis severity and a levator function at the same time.

In an example, the characteristic parameter set further includes a first distance between the pupil center point and the center point of the upper eyelid inferior margin curve, a second distance between the pupil center point and the center point of the lower eyelid superior margin curve, the palpebral fissure height between the center point of the upper eyelid inferior margin curve and the center point of the lower eyelid superior margin curve, a palpebral fissure width between the canthus left edge point and the canthus right edge point, as well as an ocular surface area derived and calculated according to the iris region. Thus, the system for detecting blepharoptosis of the present invention can achieve the effect of determining a blepharoptosis severity and a levator function with assistance of the above parameters.

In an example, according to the plurality of characteristic variables, the processing unit forms a virtual digital eye, and the processing unit is configured to overlap the virtual digital eye with each eye images to analyze whether a huge deviation is generated between the virtual digital eye and the eye image. Thus, the system for detecting blepharoptosis of the present invention can achieve the effect of improving the detection accuracy.

BRIEF DESCRIPTION OF THE DRAWINGS

The present invention is further described in detail with reference to the drawings and the specific embodiments below.

DETAILED DESCRIPTION OF THE INVENTION

In order to make the above and other objectives, characteristics and advantages clearer and more understandable, the present invention is explained in detail below according to, in particular, preferred embodiments of the present invention in cooperation with the drawings.

Figure 1:
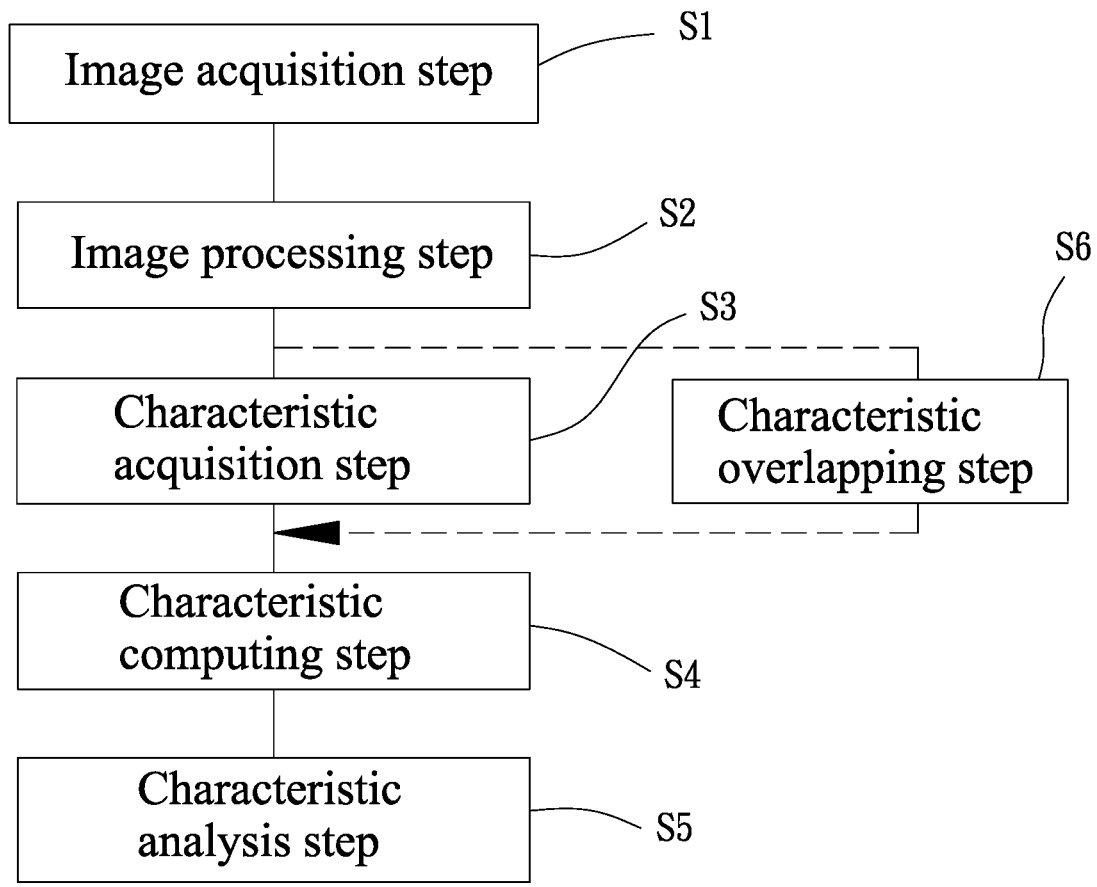
FIG. 1 is a processing flow diagram of a preferred embodiment of the present invention.

With reference to FIG. 1, a preferred embodiment of a method for detecting blepharoptosis of the present invention includes an image acquisition step S1, an image processing step S2, a characteristic acquisition step S3, a characteristic computing step S4 and a characteristic analysis step S5.

Figure 2:
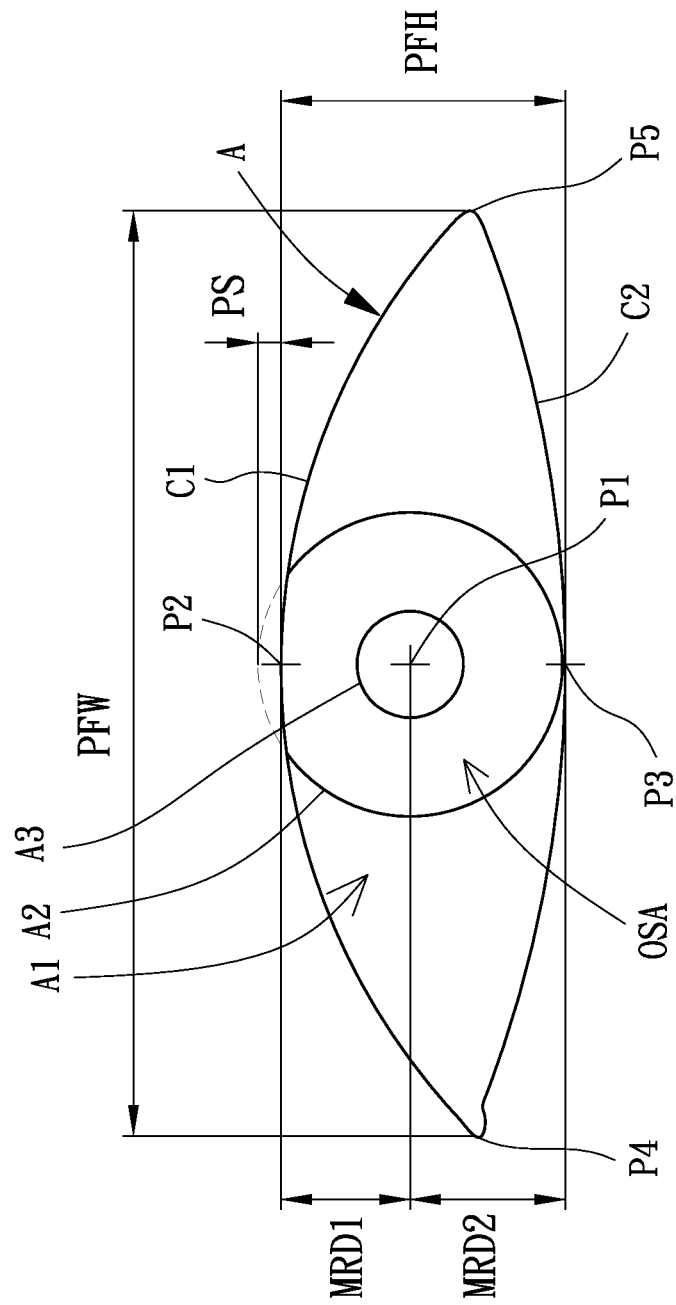
FIG. 2 is a schematic eye image diagram of a forward-looking pupil image of a preferred embodiment of the present invention.
Figure 3:
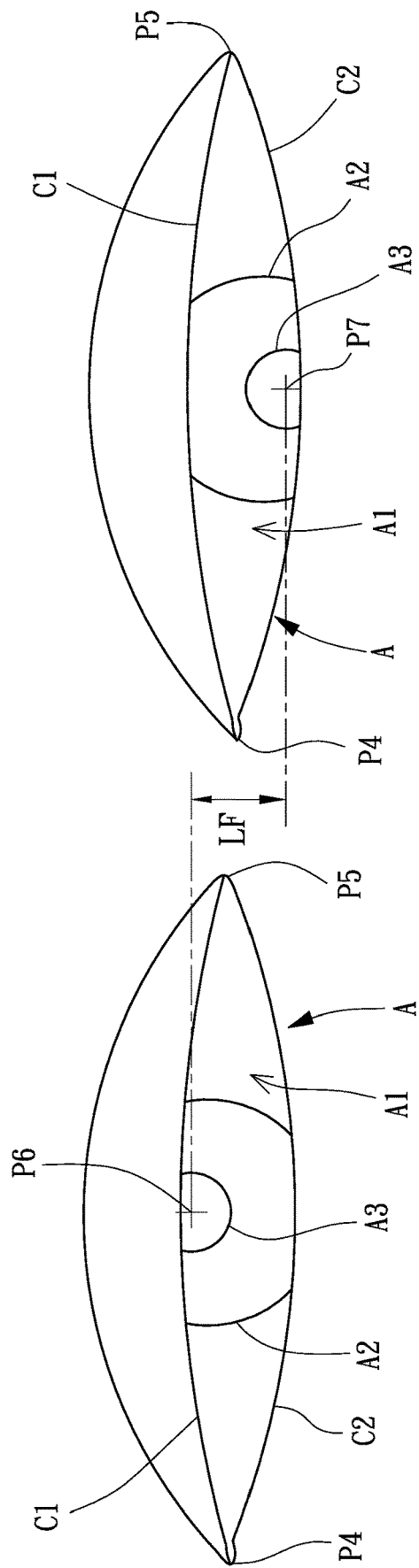
FIG. 3 is a schematic eye image diagram of pupil images gazing upward and downward to the maximum extent of a preferred embodiment of the present invention.

With reference to FIGS. 2-3 together, in the image acquisition step S1, three eye images can be generated through image capturing via a camera, with the eye images being color images. Preferably, the three eye images include a pupil image gazing forward, a pupil image gazing upward to the maximum extent, and a pupil image gazing downward to the maximum extent, respectively. Specifically, in the image acquisition step S1, a face image can be generated through image capturing via a camera, and a region of interest (ROI) is selected from the face image to serve as the eye image. A position coordinate of an initial pixel of a rectangle formed by the region of interest as well as a length value and a width value of the rectangle are set so as to cover eye positions such as an upper eyelid, a lower eyelid, a sclera, an iris and a pupil, which may be understood by a person having ordinary skill in the art and omitted herein.

In the image processing step S2, an image processing can be executed on the eye images to generate the corresponding border images. Specifically, gray-level transformation processing is executed on the eye image, so as to divide a foreground and a background of the eye image to generate a gray level image. Moreover, in the image processing step S2, a part of interest in the eye image is reserved, the image processing procedure afterwards is simplified, and an overall operation efficiency is improved. In the image processing step S2, binarization processing can be executed on the gray level image to generate a binary image. For example, but not limited hereto, a threshold value of the binarization may be distinguished as a fixed threshold value and a self-adaptive threshold value (such as Otsu, a two-peak method, a P parametric method or an iteration method). Meanwhile, in the image processing step S2, border monitoring processing can be executed on the binary image to generate the corresponding border image, so that a data size of the eye image is further greatly reduced, possibly irrelevant information is removed, and an important structure attribute of the eye image is reserved. For example, but not limited hereto, the border monitoring may use edge monitoring algorithms such as Sobel, Prewitt or Canny.

In the characteristic acquisition step S3, an image computing can be executed on the three eye images and the corresponding border images to obtain a plurality of characteristic variables for analyzing a blepharoptosis severity and a levator function. The plurality of characteristic variables include position coordinates of an eye profile region A, a sclera region A1, an iris region A2, a pupil region A3, a pupil center point P1, an upper eyelid inferior margin curve C1, a lower eyelid superior margin curve C2, center point of the upper eyelid inferior margin curve P2 and a center point of the lower eyelid superior margin curve P3, respectively. Preferably, the plurality of characteristic variables may further include respective position coordinates of a canthus left margin point P4 and a canthus right margin point P5.

Specifically, in the characteristic acquisition step S3, a symmetry transform can be executed on the eye image to obtain an eye region. The symmetry transform is executed on each pixel of the eye image to generate a plurality of symmetry transform results, and a position coordinate of a pixel of the maximum value of the plurality of symmetry transform results is used to serve as an initial point for generating the eye profile region A. The eye profile region A may include eye characteristics such as the sclera region A1, the iris region A2, the pupil region A3, an upper eyelid and a lower eyelid. Moreover, since a sclera has a lower color saturation than the eye characteristics such as a pupil, an iris, the upper eyelid and the lower eyelid, in the characteristic acquisition step S3, the eye image can be converted to an HSV color space from an RGB color space to generate an HSV image. An S channel image is obtained from the HSV image, and pixels of which saturations are lower than a threshold value in the S channel image are made to form the sclera region A1. Setting of the threshold value may be understood by the person having ordinary skill in the art and is omitted herein.

On the other hand, in the characteristic acquisition step S3, the symmetry transform can be executed on the corresponding border image to obtain a plurality of candidate pupil regions. In the present embodiment, the symmetry transform may be fast radial symmetry transform (FRST). In the characteristic acquisition step S3, two projection points of each pixel of the corresponding border image in a gradient orientation thereof are obtained through calculation, and according to an orientation projection image and a magnitude projection image formed by the two projection points respectively, a plurality of radial symmetry transform results are obtained. That is, the plurality of candidate pupil regions are obtained. Pupil black value ratios are calculated for the plurality of candidate pupil regions respectively, and the candidate pupil region with the highest pupil black value ratio serves as the pupil region A3. The pupil black value ratio is a ratio of a black pixel to all pixels of the candidate pupil region. Moreover, a position coordinate of the pupil center point P1 can be further obtained through positioning in the pupil region A3.

In the characteristic acquisition step S3, the upper eyelid inferior margin curve C1 and the lower eyelid superior margin curve C2 can be obtained in the eye profile region A. Specifically, a slope of tangent of each pixel at a boundary of the sclera region A1 with respect to the eye profile region A is calculated by a gradient orientation, and a junction, at which the slope of tangent of each pixel at the boundary of the sclera region A1 with respect to the eye profile region A is zero, is represented as an eyelid curve. According to a position coordinate of the eyelid curve, the eyelid curve is divided into the upper eyelid inferior margin curve C1 and the lower eyelid superior margin curve C2. Moreover, a horizontal plane formed by the pupil center point P1 extends toward a horizontal looking direction. A perpendicular line is perpendicular to the horizontal plane and passes through the pupil center point P1. The perpendicular line intersects with the upper eyelid inferior margin curve C1 and the lower eyelid superior margin curve C2, respectively, thereby obtaining position coordinates of the center point of the upper eyelid inferior margin curve P2 and the center point of the lower eyelid superior margin curve P3, respectively.

Preferably, in the characteristic acquisition step S3, position coordinates of the canthus left margin point P4 and the canthus right margin point P5 can be further obtained in the eye profile region A, respectively. Specifically, a junction of the upper eyelid inferior margin curve C1 and the lower eyelid superior margin curve C2 is calculated by a corner distance, and position coordinates of the canthus left margin point P4 and the canthus right margin point P5 are obtained, respectively.

With reference to FIGS. 2-3, in the characteristic computing step S4, according to the plurality of characteristic variables, a calculation can be performed to obtain a characteristic parameter set. For example, the characteristic parameter set includes a ptosis severity (PS), which is a height difference between an iris diameter and a palpebral fissure height (PFH), as well as a maximum displacement LF when a pupil moves upwards or downwards to the maximum extent. Preferably, the characteristic parameter set may further include margin reflex distance 1 MRD1 between the pupil center point P1 and the center point of the upper eyelid inferior margin curve P2, margin reflex distance 2 MRD2 between the pupil center point P1 and the center point of the lower eyelid superior margin curve P3, a palpebral fissure height (PFH) between the center point of the upper eyelid inferior margin curve P2 and the center point of the lower eyelid superior margin curve P3, a palpebral fissure width (PFW) between the canthus left margin point P4 and the canthus right margin point P5, as well as an ocular surface area (OSA) derived and calculated according to the iris region A2.

In the characteristic analysis step S5, the characteristic parameter set is compared with a preset blepharoptosis criteria information so as to derive a blepharoptosis severity and a levator function accordingly. For example, the iris diameter is obtained as 11 mm through a calculation of the iris region A2, and the palpebral fissure height (PFH) between the center point of the upper eyelid inferior margin curve P2 and the center point of the lower eyelid superior margin curve P3 is obtained as 8 mm through calculation. Thus, a ptosis severity between the iris diameter and the palpebral fissure height (PFH) is 3 mm, which means that a blepharoptosis severity is a mild degree. The preset blepharoptosis criteria information may be as shown in Table 1.

TABLE 1

Preset blepharoptosis criteria information

|  | Normal | Mild degree | Medium degree | Severe degree |
|---|---|---|---|---|
| PS | $1 \leq T_{PS} \leq 2$ | $T_{PS} = 3$ | $T_{PS} = 4$ | $T_{PS} \geq 5$ |
| LF | $T_{LF} > 12$ | $10 \leq T_{LF} \leq 12$ | $6 \leq T_{LF} \leq 9$ | $T_{LF} \leq 5$ |
| PFH | $9 \leq T_{PFH} \leq 10$ | $7 < T_{PFH} \leq 8$ | $6 \leq T_{PFH} \leq 7$ | $T_{PFH} \leq 5$ |
| MRD1 | $4 < T_{MRD1} \leq 5$ | $3 \leq T_{MRD1} \leq 4$ | $1 \leq T_{MAD1} \leq 2$ | $T_{MRD1} \leq 0$ |

The method for detecting blepharoptosis of the present invention may further include a characteristic overlapping step S6. In the characteristic overlapping step S6, according to the plurality of characteristic variables, a virtual digital eye is formed. The virtual digital eye overlaps each eye images, so that whether a huge deviation is generated between the virtual digital eye and the eye image can be analyzed. Specifically, in the characteristic overlapping step S6, a weight value can be set for each of the sclera region A1, the pupil region A3 and the eyelid curve, with a calculation formula of the weight value of the sclera region A1 being Formula (1) as shown below:

$$D_{color} = \alpha \Sigma \Delta P_{sclera} - \beta \Sigma \Delta P_{skin} \quad \text{Formula (1)}$$

In Formula (1), $P_{sclera}$ represents a pixel on a sclera; $P_{skin}$ represents a pixel on skin; and α represents a weight for controlling $P_{sclera}$, β represents a weight for controlling $P_{skin}$, and α+β=1.

A calculation formula of the weight value of the pupil region A3 may be Formula (2) as shown below:

$$D_{bia} = \frac{eye_{black}}{eye_{total}} \quad \text{Formula (2)}$$

In Formula (2), $eye_{total}$ represents all pixels of a pupil; and $eye_{black}$ represents black pixels of the pupil.

A calculation formula of the weight value of the eyelid curve may be Formula (3) as shown below:

$$D_\theta = \frac{1}{|\Omega|} \sum (x, y) \in \Omega \cos(\theta_{(x,y)} - alanm_{(x,y)})^2 \quad \text{Formula (3)}$$

In Formula (3), Ω represents a boundary of the eye profile region A; |Ω| represents a length of the boundary of the eye profile region A; $\theta_{(x,y)}$ represents a gradient orientation in a rectangular coordinate; and $m_{(x,y)}$ represents a slope of tangent of the eye profile region A.

Preferably, in the characteristic overlapping step S6, a weight value can be further set for each of the canthus left margin point P4 and the canthus right margin point P5, with calculation formulae of the weight values of the canthus left margin point P4 and the canthus right margin point P5 being Formulae (4) to (5) as shown below:

$$D_{cor} = |H| - k \cdot \text{trace}(H)^2 \quad \text{Formula (4)}$$

$$H = \sum_{(x,y)} w(x, y) \begin{bmatrix} G_x G_x & G_x G_y \\ G_x G_y & G_y G_y \end{bmatrix} \quad \text{Formula (5)}$$

In Formulae (4) to (5), w(x,y) represents a derivative value by taking a rectangular coordinate; $G_x$ represents a derivative in an x-axis orientation; $G_y$ represents a derivative in a y-axis orientation; and k represents a Harris algorithm parameter.

The above weight values serve as input variables of a weight value formula, a plurality of virtual digital eyes with different weights are obtained through calculation, and the one with the highest weight is selected from the plurality of virtual digital eyes to replace the original virtual digital eye formed by the plurality of characteristic variables. A calculation formula of the weight value may be Formula (6) as shown below:

$$\pi_p = \prod_{d_i \in \{D_\theta, D_{color}, D_{sym}, D_{cor}\}} \frac{1}{\sqrt{2\pi\sigma_i^2}} e^{-\frac{(d_i - \mu_I)^2}{2\sigma_I^2}} \quad \text{Formula (6)}$$

In Formula 6, $D_\theta$ represents the weight value of the eyelid curve; $D_{color}$ represents the weight value of the sclera region A1; $D_{sym}$ represents a weight value of the pupil region A3; $D_{cor}$ represents the weight value of an canthus margin point; $\sigma_i$ represents an optimum parameter value obtained through trial and error; $d_i$ represents separate parameter values of $D_\theta$, $D_{color}$, $D_{sym}$ and $D_{cor}$; and $\mu_I$ represents a weighted mean of $D_\theta$, $D_{color}$, $D_{sym}$ and $D_{cor}$.

Figure 4:
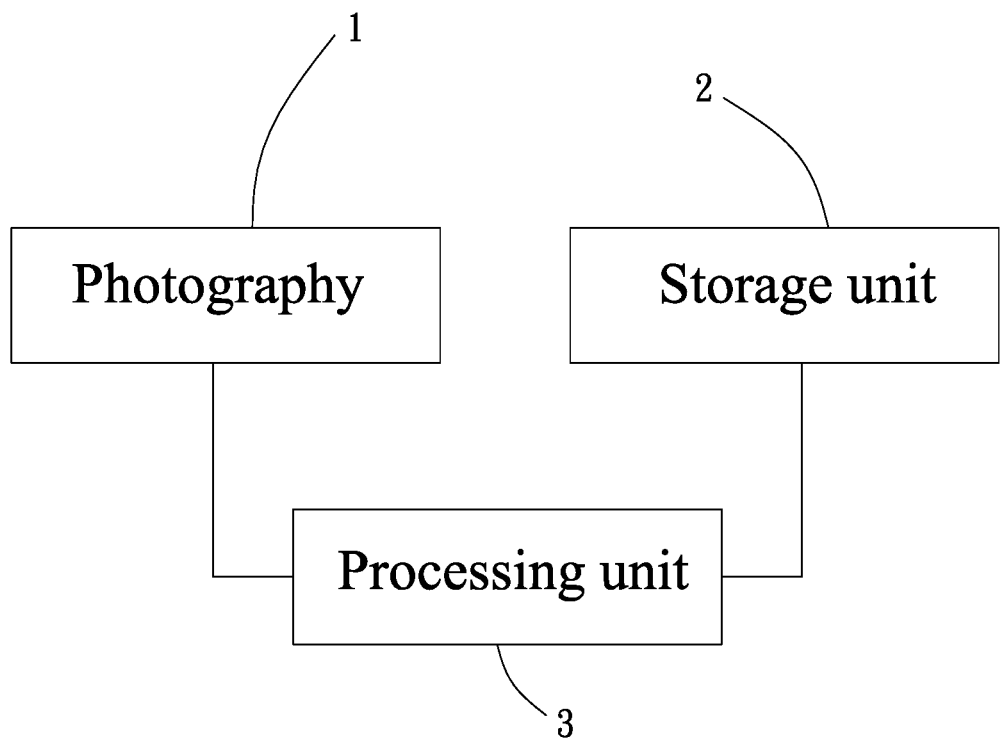
FIG. 4 is a system architecture diagram of a preferred embodiment of the present invention.

With reference to FIG. 4, a preferred embodiment of a system for detecting blepharoptosis of the present invention includes a photography unit 1, a storage unit 2 and a processing unit 3. The processing unit 3 is coupled to the photography unit 1 and the storage unit 2.

The photography unit 1 is configured to shoot to generate a face image, and preferably, generate three eye images. The three eye images may include a pupil image gazing forward, a pupil image gazing upward to the maximum extent, and a pupil image gazing downward to the maximum extent, respectively. For example, but not limited hereto, the photography unit 1 may be a charge coupled device (CCD) color camera or a complementary metal oxide semiconductor (CMOS) color camera.

The storage unit 2 may be any storage medium for storing electronic data, such as, but not limited to, a hard disk or an internal storage. The storage unit 2 is configured to store a preset blepharoptosis criteria information. The preset blepharoptosis information may be as shown in Table 1 above.

The processing unit 3 is coupled to the photography unit 1 and the storage unit 2. The processing unit 3 may be a circuit unit with functions such as data processing, signal generation and control, such as a microprocessor, a microcontroller, a digital signal processor, a logical circuit or an application specific integrated circuit (ASIC). In the present embodiment, the processing unit 3 may be, but not limited to, the microprocessor. The processing unit 3 is capable of executing an image processing on the eye images to generate the corresponding border images. Specifically, the image processing may include image processing procedures of executing gray-level transformation, binarization, edge monitoring, etc. on the eye images to generate the corresponding border images. When the photography unit 1 shoots to generate the face image, the processing unit 3 is capable of setting a region of interest in the face image to serve as the eye image. A position coordinate of an initial pixel of a rectangle formed by the region of interest as well as a length value and a width value of the rectangle are set so as to cover eye positions such as an upper eyelid, a lower eyelid, a sclera, an iris and a pupil, which may be understood by the person having ordinary skill in the art and is omitted.

The processing unit 3 is capable of executing an image computing on the eye images and the corresponding border images to obtain a plurality of characteristic variables for analyzing a blepharoptosis severity and a levator function. The plurality of characteristic variables include position coordinates of an eye profile region A, a sclera region A1, an iris region A2, a pupil region A3, a pupil center point P1, an upper eyelid inferior margin curve C1, a lower eyelid superior margin curve C2, a center point of the upper eyelid inferior margin curve P2 and a center point of the lower eyelid superior margin curve P3, respectively. Preferably, the plurality of characteristic variables may further include respective position coordinates of a canthus left margin point P4 and a canthus right margin point P5.

Specifically, the processing unit 3 executes a symmetry transform on the eye image to obtain an eye region. The processing unit 3 is capable of executing the symmetry transform on each pixel of the eye image to generate a plurality of symmetry transform results, and the processing unit 3 uses a position coordinate of the pixel of the maximum value of the symmetry transform results to serve as an initial point for generating the eye profile region A. The eye profile region A may include eye characteristics such as the sclera region A1, the iris region A2, the pupil region A3, an upper eyelid and a lower eyelid. Moreover, since a sclera has a lower color saturation than the eye characteristics such as a pupil, an iris, the upper eyelid and the lower eyelid, the processing unit 3 converts the eye image to an HSV color space from an RGB color space to generate an HSV image. The processing unit 3 obtains an S channel image from the HSV image, and pixels, of which saturations are lower than a threshold value, in the S channel image are made to form the sclera region A1. Setting of the threshold value may be understood by the person having ordinary skill in the art and is omitted.

On the other hand, the processing unit 3 executes the symmetry transform on the corresponding border images to obtain a plurality of candidate pupil regions. In the present embodiment, the symmetry transform may be fast radial symmetry transform. The processing unit 3 obtains two projection points of each pixel of the corresponding border image in a gradient orientation thereof through calculation, and according to an orientation projection image and a magnitude projection image formed by the two projection points respectively, a plurality of radial symmetry transform results are obtained. That is, the plurality of candidate pupil regions are obtained. The processing unit 3 calculates pupil black value ratios for the plurality of candidate pupil regions respectively, and the candidate pupil region with the highest pupil black value ratio serves as the pupil region A3. The pupil black value ratio is a ratio of a black pixel to all pixels of each candidate pupil region. Moreover, the processing unit 3 is further capable of obtaining a position coordinate of the pupil center point P1 through positioning in the pupil region A3.

The processing unit 3 is capable of obtaining the upper eyelid inferior margin curve C1 and the lower eyelid superior margin curve C2 in the eye profile region A. Specifically, the processing unit 3 calculates a slope of tangent of each pixel at a boundary of the sclera region A1 with respect to the eye profile region A by a gradient orientation formula, and a junction, at which the slope of tangent of each pixel at the boundary of the sclera region A1 with respect to the eye profile region A is zero, is represented as an eyelid curve. According to a position coordinate of the eyelid curve, the processing unit 3 is capable of dividing the eyelid curve into the upper eyelid inferior margin curve C1 and the lower eyelid superior margin curve C2. Moreover, the processing unit 3 is further capable of generating a horizontal plane formed by the pupil center point P1 extends toward a horizontal looking direction. The processing unit 3 makes a perpendicular line perpendicular to the horizontal plane and passes through the pupil center point P1 and makes the perpendicular line intersects with the upper eyelid inferior margin curve C1 and the lower eyelid superior margin curve C2, respectively, thereby the processing unit 3 obtaining position coordinates of the center point of the upper eyelid inferior margin curve P2 and the center point of the lower eyelid superior margin curve P3, respectively.

Preferably, the processing unit 3 is capable of obtaining position coordinates of the canthus left margin point P4 and the canthus right margin point P5 in the eye profile region A, respectively. Specifically, the processing unit 3 calculates a junction of the upper eyelid inferior margin curve C1 and the lower eyelid superior margin curve C2 according to a corner distance formula to obtain the canthus left margin point P4 and the canthus right margin point P5.

The processing unit 3 is capable of performing a calculation according to the plurality of characteristic variables to obtain a characteristic parameter set. For example, the characteristic parameter set includes a ptosis severity (PS), which is a height difference between an iris diameter and a palpebral fissure height (PFH), as well as a maximum displacement LF when a pupil moves upwards or downwards to the maximum extent. Preferably, the characteristic parameter set may further include margin reflex distance 1 MRD1 between the pupil center point P1 and the center point of the upper eyelid inferior margin curve P2, margin reflex distance 2 MRD2 between the pupil center point P1 and the center point of the lower eyelid superior margin curve P3, a palpebral fissure height (PFH) between the center point of the upper eyelid inferior margin curve P2 and the center point of the lower eyelid superior margin curve P3, a palpebral fissure width (PFW) between the canthus left margin point P4 and the canthus right margin point P5, as well as an ocular surface area (OSA) derived and calculated according to the iris region A2.

The processing unit 3 compares the characteristic parameter set with a preset blepharoptosis criteria information so as to derive a blepharoptosis severity and a levator function. For example, the processing unit 3 obtains a first position coordinate P6 through a calculation when a pupil moves upwards forcibly according to a plurality of characteristic variables generated by the pupil image gazing upward to the maximum extent, and further obtains a second position coordinate P7 through a calculation when a pupil moves downwards forcibly according to a plurality of characteristic variables generated by the pupil image gazing downward to the maximum extent. The processing unit 3 calculates a distance difference of the first position coordinate P6 and the second position coordinate P7 to generate the maximum displacement LF, and when the maximum displacement LF equals 7 mm, it means that a levator function is abnormal and in a medium degree according to the above Table 1.

According to the system for detecting blepharoptosis of the present invention, the processing unit 3 may further form a virtual digital eye according to the plurality of characteristic variables. The processing unit 3 is capable of overlapping the virtual digital eye with each eye images, so as to analyze whether a huge deviation is generated between the virtual digital eye and the eye image. Specifically, the processing unit 3 sets a weight value for each of the sclera region A1, the pupil region A3 and the eyelid curve. Preferably, the processing unit 3 is further capable of additionally setting a weight value for each of the canthus left margin point P4 and the canthus right margin point P5, and calculation formulae of the weight values may be Formulae (1) to (5) as shown above. The processing unit 3 is capable of using the above weight values to serve as input variables of a weight value formula, and obtaining a plurality of virtual digital eyes with different weights through calculation, and the processing unit 3 selects the one with the highest weight from the plurality of virtual digital eyes to replace an original virtual digital eye formed by the plurality of characteristic variables. A calculation formula of the weight value may be Formula (6) as shown above.

According to the above, the method and the system for detecting blepharoptosis of the present invention can obtain patient eye information by an image processing technology in cooperation with machine vision, derive related data for determining blepharoptosis according to the eye information, and automatically detect a levator function and a blepharoptosis severity according to the data. Thus, purposes of convenient operation, great shortening of measurement time, and improvement of measurement consistency may be achieved.

What is claimed is:

1. A method for detecting blepharoptosis, comprising:
   image capturing via a camera to generate three eye images including a pupil image gazing forward, a pupil image gazing upward to the maximum extent, and a pupil image gazing downward to the maximum extent, respectively;
   executing an image processing on the eye images to generate the corresponding border images;
   executing an image computing on the eye images and the corresponding border images to obtain a plurality of characteristic variables including position coordinates of an eye profile region, a sclera region, an iris region, a pupil region, a pupil center point, an upper eyelid inferior margin curve, a lower eyelid superior margin curve, a center point of the upper eyelid inferior margin curve and a center point of the lower eyelid superior margin curve, respectively;
   performing a calculation according to the plurality of characteristic variables to obtain a characteristic parameter set; and
   comparing the characteristic parameter set with a preset blepharoptosis criteria information to obtain a blepharoptosis severity and a levator function.

2. The method for detecting blepharoptosis as claimed in claim 1, wherein the plurality of characteristic variables further includes position coordinates of a canthus left margin point and a canthus right margin point, respectively.

3. The method for detecting blepharoptosis as claimed in claim 2, wherein the characteristic parameter set includes a ptosis severity between an iris diameter and a palpebral fissure height, as well as a maximum displacement when a pupil moves upwards or downwards to the maximum extent.

4. The method for detecting blepharoptosis as claimed in claim 3, wherein the characteristic parameter set further includes a first distance between the pupil center point and the center point of the upper eyelid inferior margin curve, a second distance between the pupil center point and the center point of the lower eyelid superior margin curve, the palpebral fissure height between the center point of the upper eyelid inferior margin curve and the center point of the lower eyelid superior margin curve, a palpebral fissure width between the canthus left margin point and the canthus right margin point, as well as an ocular surface area derived and calculated according to the iris region.

5. The method for detecting blepharoptosis as claimed in claim 2, wherein according to the plurality of characteristic variables, a virtual digital eye is formed, and the virtual digital eye overlaps each eye image to analyze whether a huge deviation is generated between the virtual digital eye and the eye image.

6. A system for detecting blepharoptosis, comprising:
   a photography unit configured to capture three eye images including a pupil image gazing forward, a pupil image gazing upward to the maximum extent, and a pupil image gazing downward to the maximum extent, respectively;
   a storage unit configured to store a preset blepharoptosis criteria information; and
   a processing unit coupled to the photography unit and the storage unit, wherein the processing unit executes an image processing on the eye images to generate the corresponding border images, the processing unit executes an image computing on the eye images and the corresponding border images to obtain a plurality of characteristic variables, and the processing unit performs a calculation according to the plurality of characteristic variables to obtain a characteristic parameter set, and compares the characteristic parameter set with the preset blepharoptosis criteria information to obtain a blepharoptosis severity and a levator function, wherein the plurality of characteristic variables includes position coordinates of an eye profile region, a sclera region, an iris region, a pupil region, a pupil center point, an upper eyelid inferior margin curve, a lower eyelid superior margin curve, a center point of the upper eyelid inferior margin curve and a center point of the lower eyelid superior margin curve, respectively.

7. The system for detecting blepharoptosis as claimed in claim 6, wherein the plurality of characteristic variables further includes position coordinates of a canthus left margin point and a canthus right margin point, respectively.

8. The system for detecting blepharoptosis as claimed in claim 7, wherein the characteristic parameter set includes a ptosis severity between an iris diameter and a palpebral fissure height, as well as a maximum displacement when a pupil moves upwards or downwards to the maximum extent.

9. The system for detecting blepharoptosis as claimed in claim 8, wherein the characteristic parameter set further includes a first distance between the pupil center point and the center point of the upper eyelid inferior margin curve, a second distance between the pupil center point and the center point of the lower eyelid superior margin curve, the palpebral fissure height between the center point of the upper eyelid inferior margin curve and the center point of the lower eyelid superior margin curve, a palpebral fissure width between the canthus left margin point and the canthus right margin point, as well as an ocular surface area derived and calculated according to the iris region.

10. The system for detecting blepharoptosis as claimed in claim 7, wherein according to the plurality of characteristic variables, the processing unit forms a virtual digital eye, and the processing unit is configured to overlap the virtual digital eye with each eye images to analyze whether a huge deviation is generated between the virtual digital eye and the eye image.

* * * * *